United States Patent [19]

Saferstein et al.

[11] Patent Number: 4,616,644
[45] Date of Patent: Oct. 14, 1986

[54] HEMOSTATIC ADHESIVE BANDAGE

[75] Inventors: Lowell Saferstein, Edison; Julius A. Lindquist, Bridgewater; Stephen J. Wolf, Manville, all of N.J.

[73] Assignee: Johnson & Johnson Products, Inc., New Brunswick, N.J.

[21] Appl. No.: 744,829

[22] Filed: Jun. 14, 1985

[51] Int. Cl.$^4$ ............................................. A61L 15/00
[52] U.S. Cl. .................................................... 128/156
[58] Field of Search ....................... 128/156, 155, 268

[56] References Cited

U.S. PATENT DOCUMENTS

| 3,434,472 | 3/1969 | Hérnlman | 128/156 |
| 4,212,296 | 7/1980 | Schaar | 128/156 |
| 4,233,969 | 11/1980 | Lock | 128/156 |
| 4,292,299 | 9/1981 | Suzuki | 128/156 |
| 4,292,972 | 10/1981 | Pawelchak | 128/156 |

Primary Examiner—Gregory E. McNeill

[57] ABSTRACT

Hemostatic adhesive bandages are disclosed wherein a very thin coating of a high molecular weight polyethylene oxide is applied to the surface of the perforated plastic film wound release cover of an adhesive bandage, in a manner compatible with commonly used high speed production techniques and equipment, which stop the bleeding faster when applied to minor cuts.

10 Claims, 3 Drawing Figures

U.S. Patent     Oct. 14, 1986     4,616,644
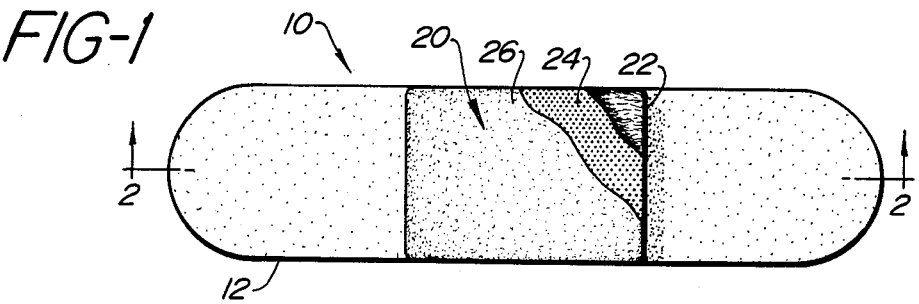
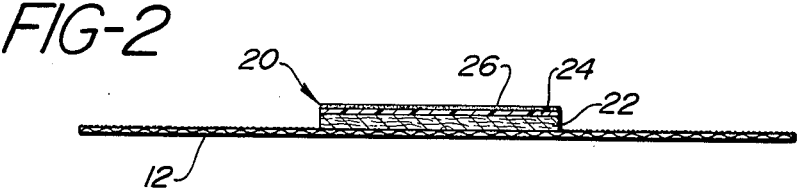
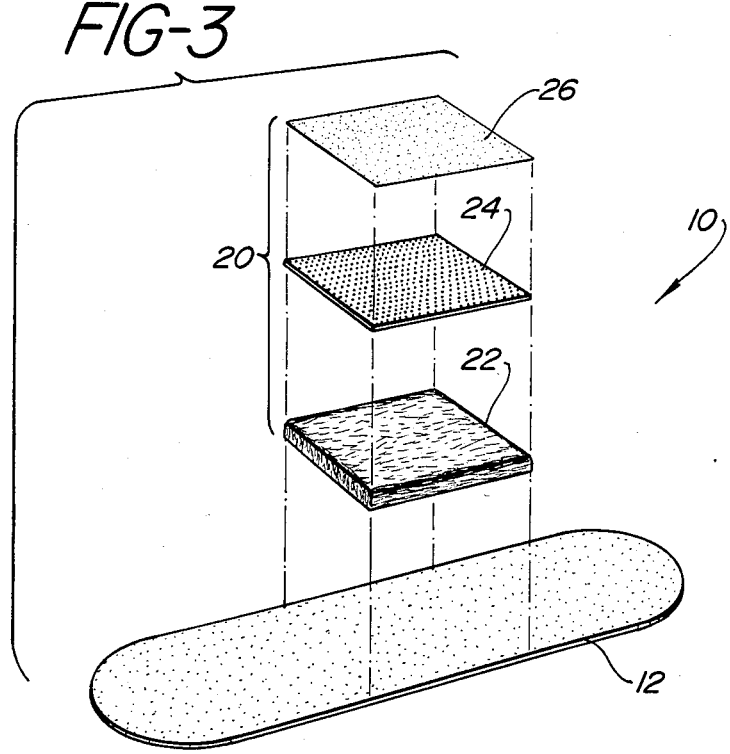

HEMOSTATIC ADHESIVE BANDAGE

BACKGROUND OF THE INVENTION

This invention relates to adhesive bandages comprising a surgical adhesive tape backing on which is an absorbent pad having a perforated film-type nonadherent wound release cover, and is more particularly concerned with such adhesive bandages in which the wound release cover is coated with a very thin layer of a high molecular weight polyethylene oxide to improve the hemostatic effect of such adhesive bandages when applied to minor cuts, abrasions and puncture wounds.

Adhesive bandages having a nonadherent wound release cover in the form of a perforated plastic film which are useful in the present invention are disclosed in U.S. Pat. No. 3,434,472 (Smith & Nephew Ltd.) and are well-known commercially available materials, e.g., from Johnson & Johnson as BAND-AID* Brand Adhesive Bandages (containing a non-stick cushion pad) in the form of sheer strips, patches, spots, plastic strips; from Colgate-Palmolive Co. (Kendall) as Curity CURAD* "Ouchless" Adhesive Bandages, and from American White Cross Laboratories, Inc. as STIK-TITE* elastic strips. Other useful perforated film type nonadherent wound release cover surfaces suitable for use in the present invention are taught in U.S. Pat. No. 3,285,245 (Minnesota Mining and Manufacturing Company) and in U.S. Pat. No. 2,923,298 (The Kendall Company). In all of these adhesive bandages, the wound release cover is very thin, usually less than 10 mils thick.

These known adhesive bandages, are commonly applied with slight pressure to minor cuts, abrasions and puncture wounds where they aid in stopping the bleeding, as well as in protecting the wound from contamination. While these adhesive bandages work reasonably well, it would be highly desirable if they could also have an improved hemostatic which could be obtained conveniently, inexpensively, and in a manner compatible with the various high-speed production tecniques and equipment commonly used to make such adhesive bandages on a commercial scale.

SUMMARY OF THE INVENTION

Improved hemostatic adhesive bandages have been sought for many years. We have unexpectedly found that the application of a very thin coating of polyethylene oxide having a molecular weight above about 600,000 Daltons to the surface of the wound release cover substantially increases the hemostatic effect when the adhesive bandage is applied to minor cuts, abrasions and puncture wounds to stop the bleeding faster, without changing its wound release characteristics. Comparing the hemostatic effect of a commercially-available adhesive bandage which has a polyethylene non-woven net wound release cover surface with a comparable adhesive bandage of the present invention which differed only in having an approximately five percent add-on, based on the weight of the non-woven net, of polyethylene oxide which has an approximate molecular weight of 4,000,000, the hemostatic adhesive bandage of the present invention stopped bleeding of a minor cut about one-third faster. Where the polyethylene oxide used has a higher molecular weight, even less of an add-on is needed to attain a comparable hemostatic effect. "Polyethylene oxide", which is used in the present invention, is also referred to as poly(ethylene oxide), or as polyoxyethylene polymer or resin, or as 1,2 epoxide polymer, or as Polyox, or by various other synonyms, and is included within the CAS Registry Number 25322-68-3. The particular polyethylene oxides useful here are high molecular weight polymers with average molecular weights from 600,000 and higher.

The Prior Art Distinguished

Anderson U.S. Pat. No. 3,328,259 (assigned to Parachem Corporation) entitled "Dressing for a Wound Containing a Hemostatic Agent" describes making a dressing for a wound containing a hemostatic agent using a cellulose derivative, particularly the sodium salt of carboxymethyl cellulose for that purpose. This patent says that polyoxyethylene (Polyox) is an equivalent for the cellulose derivative specifically described, but gives no specific details of how the Polyox is to be used. If the polyoxyethylene were to be substituted for the cellulose derivatives described in said prior art patent, there are a great many differences between that dressing and the hemostatic dressing of the present invention. Thus, said prior art patent calls for a "film-like bandage" where the film is relatively thick on the order of 1–6 mils, whereas in the present invention the polyoxyethylene is not used in the form of a film, but rather in the form of a very thin coating (which normally would be less than 0.1 mils), and which coating may not even be a solid coating, but could be a porous coating since the perforated film wound release cover substrate to which it is applied contains openings which may not all be bridged after the polyoxyethylene is coated thereon. The prior art film remains as a film when applied to the wound, whereas the very thin coating of polyoxyethylene of the present invention upon application to a wet wound instantly dissolves and no longer exists as a film but rather as a viscous solution. The prior art film is much thicker than any reinforcing backing which it may contain, while in the present invention the polyoxyethylene coating is much thinner than the wound release surface, to which it is applied. The prior art thick film always contains a plasticizer, which is not needed (but could be used) for the purposes of the present invention. The prior art patent also is not concerned with an adhesive bandage or with a bandage designed for use for the type of wounds to which the adhesive bandages of the present invention will be used, but rather is concerned with a bandage used in a different way for a different purpose, and which requires that the film from the wound be removed from the wound by treatment with water in order not to disturb the wound in any way, while the hemostatic adhesive bandage of the present invention is merely pulled off in the normal manner and just does not adhere to the wound.

King, U.S. Pat. No. 3,419,006, teaches a dressing utilizing a layer of a hydrophilic polymer gel made from cross-linked poly(ethylene oxide). Such a dressing is quite different in construction, size and operation from the adhesive bandage of the present invention which does not utilize the cross-linked form of poly(ethylene oxide) and does not utilize any hydrophilic polymeric gel. In fact, a commercial form of the dressing of the King patent, available as SPENCO 2nd SKIN Dressing (Spenco Medical Corporation) [and also as VIGILON ® Brand Primary Wound Dressing, (C. R. Bard Inc.)], did not have as much of a hemostatic effect when tested, as did a plain prior art type adhesive bandage control. These dressings, which are 40 mils thick, are gels of a colloidal suspension of radiation-cross-linked polyethylene oxide (4%) and water (96%) on a polyethylene mesh support. They are just not applicable for use as, or in place of, the hemostatic adhesive bandages of the present invention.

DESCRIPTION OF DRAWINGS

FIG. 1 is a plan view illustrating a hemostatic adhesive bandage of the present invention with certain portions shown in cut-away fashion.

FIG. 2 is a cross-sectional view taken along line 2—2 of FIG. 1.

FIG. 3 is an exploded perspective view of the adhesive bandage of FIG. 1.

DETAILED DESCRIPTION OF THE INVENTION

The hemostatic adhesive bandages of the present invention comprise an adhesive bandage of the medical or surgical type, including an adhesive strip having attached thereto an absorbent pad bandage portion covered with a perforated plastic film non-adherent wound release cover which wound release cover has been coated with a very thin coating of a hemostatic agent comprising a high molecular weight polyethylene oxide.

The drawings all illustrate the same typical embodiment of the hemostatic adhesive bandage 10, in which the adhesive coated backing 12 has affixed to it an absorbent pad structure 20 having an absorbent pad 22 covered by a perforated film-type non-adherent wound release cover 24 which is coated with a very thin coating of a high molecular weight polyethylene oxide 26. The polyethylene oxide coating 26 may or may not have openings corresponding to those on the release cover 24.

Not shown, but which will normally be utilized in actual use, are two strips of release paper (such as a silicone-coated release paper or other alternate materials which can be readily removed at the time of use), which are applied so as to cover, in an overlaying manner, the entire adhesive side of the hemostatic adhesive bandage. Also not shown, but which will be normally used, is an individual sealed package made of glassine-paper or a similar bacterial barrier material into which each hemostatic adhesive bandage is placed before it undergoes ethylene oxide sterilization so as to maintain sterility until the adhesive bandage is ready for use. At that time, the user would open the sterile package, remove the hemostatic adhesive bandage, remove the two strips of release paper and apply the polyethylene oxide coating 26 side of the absorbent pad structure 20 to the wound and then the adhesive end portions to the skin to hold the entire structure in place.

The distinction between prior art adhesive bandages and the hemostatic adhesive bandage of the present invention is in the added presence of the polyethylene oxide coating 26. Thus, the usual prior art methods of manufacture applicable to the prior art adhesive bandages and to the various materials and ingredients used therein may be used here also, except that irradiation sterilization, e.g., with Cobalt 60, should not be used since it will cross-link the polyethylene oxide and render it non-hemostatic. Steam sterilization should not be used either. Instead, the widely used ethylene oxide method of sterilization can be used.

While the drawings illustrate one shape, the hemostatic adhesive bandages may take any shape in which the prior art non-hemostatic adhesive bandages may be made.

The adhesive backing 12, may be made from any cloth or plastic type fabric coated with any pressure-sensitive adhesive which is customarily used on the prior art non-hemostatic adhesive bandages.

The Polyethylene Oxide

The present invention requires the use of polyethylene oxide as a thin coating for a perforated plastic film wound release surface, for the preparation of a hemostatic adhesive bandage. We have found, unexpectedly, that very small quantities of polyethylene oxide are very effective in reducing the bleeding time of minor wounds, the polyethylene oxide being employed as a very thin coating on a porous plastic substrate, i.e., on the release pad of an adhesive bandage.

The polyethylene oxide resins useful for the present invention are not crosslinked to form a gel as occurs when the polyethylene oxide is irradiated. It should be understood that the term "polyethylene oxide", when used in describing and claiming. the present invention, refers only to the non-irradiated, non-crosslinked, non-gel forms thereof.

Polyethylene oxide resins are made commercially by the catalytic polymerization of ethylene oxide in the presence of any one of several different metallic catalyst systems. They are currently available [from Union Carbide Corporation (U.S.) as "Polyox", from Meisei Chemical Works Ltd. (Japan) as "Alkox" and from Seitetsu Kagaku Co. Ltd. (Japan) as "PEO"with average molecular weights from as low as 200 to up to 7 million. However, those products with a molecular weight below 25,000 are viscous liquids or waxy solids, commonly referred to as polyethylene glycols. The polyethylene oxide resins which are useful for the present invention have a molecular weight range from 600,000 to 7,000,000, and even higher, should such materials later become available. They are dry, free flowing, white powders completely soluble in water at temperatures up to 98° C. and completely soluble in certain organic solvents. They have crystalline melting points from 63° to 67° C. Above the crystalline melting point the resins become thermoplastic materials which can be formed by molding, extrusion or calendering. Aqueous solutions display increasing pseudoplasticity and pituitousness as the molecular weight of the resin increases.

Because the paired ether-oxygen electrons in these polymers have a strong affinity for hydrogen bonding, polyethylene oxide resins form association complexes with a wide variety of monomeric and polymeric organic compounds as well as certain inorganic electrolytes.

Thus, for example, polyethylene oxide forms association compounds with proteins such as gelatin, polyureas and organic compounds like urea and thiourea.

While we do not wish to be bound by any particular theory of how our invention works, it is postulated that the combination of the very high viscosity that small amounts of polyethylene oxide can impart to water along with its ability to form association compounds with certain proteins, is responsible for the hemostatic property of these polymers. We speculate that when an adhesive bandage containing a small amount of polyethylene oxide resin is placed on a bleeding surface the resin rapidly dissolves in the aqueous plasma of the blood and thereby immediately increases the viscosity of the plasma. At the same time, blood proteins, such as prothrombin and fibrinogen, begin to associate with the polyethylene oxide molecules thus increasing the local concentration of these proteins and effecting more rapid interaction among them, compared to the normal diffusion controlled reactions in the absence of the polyethylene oxide. Thus, the increase in viscosity of the plasma which slows the flowing blood and the concentrating of the essential blood proteins at the surface of the polyethylene oxide molecules are postulated to be the mechanism for the hemostatic efficacy of polyethylene oxide.

In order for the polyethylene oxide molecules to bring about quick hemostasis we have found it necessary for the polymer to rapidly dissolve in the plasma of the blood issuing forth from the cut or wound site. This is achieved readily if the polyethylene oxide is in the form of a very thin film coating on the surface of the adhesive bandage. The polyethylene oxide thin coating could be on either surface of the release cover, but preferably is on the side of the surface closest to the wound.

While the polyethylene oxide is the key hemostatic material, other water-soluble polymers may be added to the polyethylene oxide without appreciably diminishing the hemostatic activity of the polyethylene oxide, and such mixtures are to be regarded as the full equivalents of the polyethylene oxide itself for purposes of the present invention, the other added water-soluble polymer or polymers being merely a diluent. In any such mixture, the major component preferably should be the polyethylene oxide, but there could be present up to 50 weight percent [based on the weight of all the polymers, including the polyethylene oxide] of one or more other water-soluble polymers. Good demonstrated results have been obtained with mixtures of polyethylene oxide and sodium carboxymethyl cellulose (50:50) and mixtures of polyethylene oxide and polyvinyl pyrrolidone (50:50). Representative of the many other water-soluble polymers useful for this purpose are the alkyl celluloses, hydroxyalkyl celluloses, polyvinyl alcohol, polyacrylamide aad partially hydrolyzed polyacrylamides, and various naturally-occurring gums such as guar, alginates, xanthan and similar materials.

Also, while the use of plasticizers with the polyethylene oxide is not preferred or necessary for purposes of the present invention, water-soluble plasticizers, such as glycerine, polyethylene glycol and the like, optionally may be added if desired.

Where it is desired to include another water-soluble polymer or polymers and/or a water-soluble plasticizer, this can be done by adding these water-soluble materials to the polyethylene oxide solution before it is coated onto the wound release surface.

We have found that the use of the above water-soluble polymers and water-soluble plasticizers as diluents does not significantly adversely affect the hemostatic activity of the polyethylene oxide. The properties of the very thin coating placed on the release cover remain about the same as with polyethylene oxide alone, and the material still processes well on high speed adhesive bandage making equipment.

The Wound Release Surface

Many known commercially produced adhesive bandages contain a thin perforated plastic film atop the absorbent pad. The plastic film functions as a wound release cover surface so that when the bandage is removed the scab will not be disrupted and reinitiate bleeding.

This wound release cover can be made of a plastic material, of which the most commonly encountered examples are polyethylene, polypropylene, polyesters and nylon. The plastic film is perforated in different ways which all serve to provide small openings for the blood to enter the absorbent pad beneath the perforated film. This plastic release surface can also be a woven, knitted, or non-woven structure, so long as it contains apertures sufficient to permit the blood to flow into the absorbent pad. Representative examples include materials such as Delnet film of polyethylene and Telfa film of polyester.

Illustrative of various preferred non-adherent wound release covers are those available from Hercules as one of their series of Delnet light weight, non-woven fabrics made from high-density polyethylene or polypropylene through a process of extrusion, embossing and orientation. These have weights of about 0.36–1.06 oz/yd$^2$, a thickness of about 4–10.5 mils, and an open area of 17–46%. In particular, we prefer to use Delnet P-530, which is a high density polyethylene of a weight of 0.55 oz/yd$^2$ a thickness of 4.3 mils and an open area of 34%, and which material was utilized in those examples where no other material was specified.

The Coating Operation

We have found, as part of this invention, that coating the wound release cover with a very thin coating of polyethylene oxide (much thinner then the release cover) is a very effective method for getting the polyethylene oxide to the bleeding site.

It makes no difference whether the perforated plastic release cover is coated first and then attached to the absorbent pad of the bandage or if the release film is first attached to the absorbent pad (as in a unitized pad) and the whole entity is then coated with a polyethylene oxide solution to produce a thin coating or film on the release film.

During the coating operation, some or all of the perforated holes in the plastic release cover may be bridged with a thin coating of polyethylene oxide. Since the coating or film is so thin (<0.1 mils) it dissolves immediately upon becoming wetted with plasma from the blood. Thus the perforated holes are not blocked by this hemostatic polymeric coating or film.

In order to coat the release cover with polyethylene oxide, the polyethylene oxide polymers found effective in this invention [which range in molecular weight from 600,000 to 7 million or higher if available], are solubilized by dissolving them in various solvents or mixtures of solvents.

The concentration of the polymer in the solvent can range from a low of 0.5% to a high of 6.5%, but most preferred are 2.0% to 3.0% for polyethylene oxide having a M.W. of 4,000,000 and 1.0% to 2.0% for polyethylene oxide having a M.W. of 7,000,000. Typical of the various solvents which may be used are water, water-methyl alcohol mixtures, isopropyl alcohol, benzene, acetone and methylene dichloride, but the possible solvents are not limited to those mentioned above.

Alternatively, since polyethylene oxide is a low temperature melting thermoplastic polymer, it can also be extruded as a melt into a thin film directly onto the absorbent pad or the release film.

Our preferred method is the solvent coating of the polyethylene oxide polymer directly on the wound release cover or directly onto the absorbent pad where the nature of the absorbent pad is such that it does not require a separate wound release cover because the wound release cover previously was built into the absorbent pad structure itself, i.e., a unitized pad.

The coating operation to apply the polyethylene oxide is conducted most preferably with a reverse roll coater. The type of coater is not a part of this invention and is only mentioned as an example of one type of coating technology that has been put into practice. Many types of coating technology and equipment are applicable for use in making the hemostatic bandages of this invention.

More important than the type of coater is the amount of high molecular weight polyethylene oxide applied to the adhesive bandage. We have found that an increase in weight of the porous polymeric wound release cover of 1-10% is sufficient to produce a significant hemostatic effect.

The most preferred add-on increase is 3-8% for the 4,000,000 M.W. polyethylene oxide, and 2-6% for the 7,000,000 M.W. polyethylene oxide of the original weight of our Delnet polyethylene wound release film. These addon amounts are so small that they are difficult to detect with the naked eye.

The hemostatic adhesive bandages of the present invention are made using the same high-speed production techniques and equipment as are used for commercially available non-hemostatic adhesive bandages. Since the inventive feature is in the polyethylene oxide coating on the wound release cover, the Examples below illustrate that aspect of the invention.

EXAMPLE 1

Into a large pail add 29.28 kilograms of isopropyl alcohol. While stirring rapidly, add 0.90 kilograms of polyethylene oxide (Union Carbide's Polyox Resin WSR-301, molecular weight 4,000,000). The polymer disperses in the alcohol but does not dissolve. Add 5.82 kilograms of distilled water and stir slowly for 15 minutes. The polyethylene oxide rapidly dissolves as the water is added. This procedure produces a 2.5% Polyox solution concentration with a Brookfield viscosity of 15,433 cps using spindle No. 1 at 1 rpm. The solution is 81.33% by weight in isopropyl alcohol and 16.16% by weight in water.

This solution is coated onto a net-like perforated polyethylene film known as Delnet P-530 produced by Hercules, Inc. The Polyox solution is coated onto the Delnet with a reverse roll coater. After the Delnet is coated with a thin film of the Polyox solution, the coated Delnet film passes through warm ovens to evaporate off the solvents leaving a very light film of polyethylene oxide coated on the Delnet film which is then rolled up. The weight increase of the Delnet was 8.1%.

The coated Delnet roll is attached to an absorbent pad made of wood pulp, which is then cut and attached to an adhesive-coated backing, all by high speed machinery well-known to those skilled in the art of making adhesive bandages. The coated Delnet P-530 processes through the machinery with no problems and produces hemostatic adhesive bandages that are virtually indistinguishable from regular bandages in every aspect, except for the bleeding time measured on a cut. Thus, for example, adhesive bandages made by the process of this example exhibited, an average bleeding time on rabbit ear cuts (a model for human cuts) of 49 seconds versus a control of 83 seconds. (The control is an identical adhesive bandage but uncoated with Polyox).

EXAMPLE 2

Into a large bucket charge 1,187.5 grams methyl alcohol. With rapid stirring add 125 grams of polyethylene oxide (Union Carbide Polyox Resin WSR-205, molecular weight 600,000). The polyethylene oxide disperses but does not dissolve. Add 1,187.5 grams distilled water and reduce the stirring speed as the polymer dissolves and the viscosity increases after 20 minutes of stirring. The 5% solution of Polyox resin WSR-205 in 47.5% methyl alcohol, 47.5% water is ready for coating. This solution exhibits a Brookfield viscosity of 5701 cps using a No. 1 spindle at 1 rpm.

This resin is coated onto Delnet P-530 film in a manner described in Example 1. A very thin film of polyethylene oxide is layed down by this process on the perforated Delnet polyethylene film. The uncoated Delnet P-530 film has a weight of 0.450 oz. per square yard. The Polyox add-on was 0.027 oz. per square yard or a 6% increase over original weight.

This coated Delnet film is manufactured into adhesive bandages by machinery which, at high speeds, attaches the coated Delnet to the absorbent pad which comprises the bandage. The machinery used is the same high speed commercial equipment used to make the prior art non-hemostatic adhesive bandages. The bandages are sterilized with ethylene oxide with no damage to the hemostatic coating. When the above bandages were tested on a rabbit ear bleeding model, the average bleeding time for the hemostatic bandage was 60 seconds versus 86 seconds for the uncoated control.

EXAMPLE 3

This example illustrates the application of polyethylene oxide resin to a unitized pad. This unitized pad is one in which the porous plastic film or release cover surface is prebonded to the absorbent pad which is a composite of 90% polypropylene, 10% rayon. Thus, the Delnet P-530 film is prebonded to the 90/10 pad and the polyethylene oxide resin is coated directly onto the surface of this material.

A 2.0% solution of Polyox WSR-301 (molecular weight 4,000,000) is prepared in a mixed solvent of 58.8% methyl alcohol, 39.2% water. This solution has a viscosity of 8,552 centipose using a Brookfield viscometer with a No. 1 spindle at 1 rpm.

The solution of polyethylene oxide (Polyox WSR-301) is coated onto the unitized pad with a reverse roll coater. A thin film of polyethylene oxide forms on the surface of the Delnet bonded to the 90/10 absorbent pad. The unitized pad weighs 3.145 oz. per sq. yard. The coated pad weighs 3.172 per sq. yard, or a pick up of 0.027 oz. per sq. yard, or 0.85% increase based on entire pad, or 6% increase based on the Delnet film only. This material is converted into adhesive bandages by well known commercially available equipment and technology normally used for non-hemostatic adhesive bandages. When these bandages were tested on a bleeding rabbit ear model they exhibited a bleeding time average of 48 seconds for the hemostatic bandage versus 72 seconds for the uncoated control with a standard deviation of 17.

EXAMPLE 4

A 2% solution of Polyox WSRN-60K (molecular weight 2,000,000) is prepared in a mixed solvent consisting of 58.8% by weight water and 39.2% by weight methyl alcohol. This solution exhibits a Brookfield viscosity of 4,030 cps with a No. 1 spindle at 1 rpm.

This solution is coated onto a Delnet perforated polyethylene film and then passed through an oven to evaporate the solvents. The weight add-on to the Delnet is 8.0%. The thickness of this film is less than 0.1 mils. The coated Delnet is manufactured into adhesive bandages by high speed machinery which attaches the Delnet to an absorbent pad. These bandages, when tested for bleeding times, stopped bleeding faster by 40% in the time compared to an uncoated control.

EXAMPLE 5

This example illustrates the effect of polyethylene oxide on a polyester perforated film called Telfa [which is used commercially on bandages available from Colgate-Palmolive as Curity Telfa adhesive pads].

A 2.0% by weight of Polyox WSR-301 in a solution of 58.8% methyl alcohol, 39.2% water was coated onto a perforated polyester film called Telfa with the help of a draw knife. A very thin film, 0.1 mil, of polyethylene oxide was laid down on the polyester surface. The coated Telfa film was placed over an absorbent pad and this makeshift bandage was tested on the bleeding ear of a rabbit. The bleeding times of this hemostatic bandage were 30% shorter than an otherwise identical but uncoated control.

EXAMPLE 6

Into a large pail is added 1,773 grams methyl alcohol. While stirring add 45 grams Polyox WSR-303, mol. wt. 7 million. The Polyox Resin does not dissolve but disperses in the methanol. While stirring add 1,182 grams of water and stir for 1 hour. This procedure produces a 1.5% Polyox solution in 39.4% water, 59.1% methyl alcohol. The viscosity of this solution is 11,100 cps measured on a Brookfield viscometer using Spindle No. 1 at one rpm.

This solution is coated onto Delnet P-530 with a reverse roll coater. The coated Delnet passes through a warm oven to evaporate off the solvent. The weight percent increase of the Delnet is 3.5%.

The coated Delnet roll is attached to an absorbent pad made of wood pulp, and made into adhesive bandages. These bandages, when tested for hemostasis, stop bleeding on a rabbit ear model in 52 seconds versus a control of 85 seconds.

EXAMPLE 7

Into a large pail add 1,746 grams methyl alcohol and 60 grams Polyox WSR-301. Into another pail dissolve 30 grams of sodium carboxymethyl cellulose #7H3SCF trom Hercules Incorporated in 1,164 grams water. Stir this solution for 2 hours, then add the aqueous polymer solution to the stirring suspension of Polyox in methyl alcohol. Stir the resulting solution for 2 hours. This polymer solution exhibits a Brookfield viscosity of 64,000 cps; and consists of 2.0% Polyox WSR-301, 1.0% CMC, 38.8% water and 58.2% methyl alcohol.

This solution is coated onto Delnet and the solvent evaporated off in a warm oven. The percent add on is 7.5%.

When this coated Delnet is made into adhesive bandages, these bandages exhibit a bleeding time of 50 seconds compared to a control of 80 seconds.

EXAMPLE 8

Into a large pail, add 1,746 grams methyl alcohol. To this with stirring add 40 grams of Polyvinylpyrrolidone K-90 from GAF Corporation. Stir this solution until the PVP is dissolved. Add to this solution 40 grams of Polyox WSR-301 and while stirring add 1,104 grams water. Continue stirring for 1 hour. This procedure produces a polymer solution with a concentration of 1.36% in PVP, 1.36% in Polyox, 59.6% in methyl alcohol and 37.7% in water.

The viscosity of this solution is 8,800 cps measured with a Brookfield viscometer using Spindle No. 1 at one rpm.

This solution is coated onto Delnet and the solvent evaporated off in a warm oven. The weight percent increase to the Delnet is 5.0%. This coated Delnet is made into adhesive bandages as previously described. When tested for hemostasis, these bandages stop bleeding on a rabbit ear model in 58 seconds, versus a control of 83 seconds.

EXAMPLE 9

Into a large pail equipped with a stirrer add 1,176 grams methyl alcohol. While stirring add 40 grams of Polyox coagulant grade mol. wt. 5 million. Stir for a few minutes, then add 784 grams water and stir for 1 hour. This procedure produced a 2.0% solution of coagulant grade Polyox in 58.8% methyl alcohol and 39.2% water.

This solution exhibits a Brookfield viscosity of 7,300 cps using a Number 1 Spindle at one rpm. This solution is coated onto Delnet using a reverse roll coater and the solvent evaporated off in a warm oven. The add on to the Delnet is 6.0%. When the coated Delnet is manufactured into adhesive bandages, these bandages exhibit a bleeding time of 53 seconds versus 85 seconds for tne control when tested on a rabbit ear model.

TEST PROCEDURE FOR HEMOSTASIS

The hemostasis effect of the dressings of the present invention (as shown in the preceding Examples 1-5) was evaluated by the following rabbit ear hemostasis test which simulates, in a laboratory, the type of minor cuts that adhesive bandages are often used on.

The test procedure is as follows:

1. Inject each rabbit I.M. with "Rabbit Magic" anesthetic at a dosage of 1 cc per 5 lbs of body weight. The "Rabbit Magic" must be made fresh daily:
   1 cc ROMPUN (20 mg/ml)
   2 cc Ketamine Hydrochloride (100 mg/ml)
   1 cc Saline or $H_2O$ 2. Shave the medial marginal vein on both ears. Place ear on a hard, flat surface and make an incision with a razor blade across the entire width of the vein, being careful not to completely transect the vein. Be sure the segment of vein selected is of consistent and fairly large diameter.

3. Wipe the first bit of blood off the incision with a gauze sponge and observe the wound site for adequate, but not profuse, blood flow. Wipe the incision once again with a gauze sponge and immediately cover the incision with an adhesive bandage sample (clear or sheer backing) perpendicular to the vein and simultaneously start a stopwatch. Hold thumb on the sample over the wound site with slight pressure for 5 seconds to assure adequate contact between sample and incision.

4. When all visible bleeding has stopped, record the time in seconds for the hemostatic time. If sample saturates before hemostasis occurs, discard sample, record as saturated and repeat Steps 2 and 3 with a new sample.

5. Make a second incision on the same ear within the originally chosen segment and test as above. Make 2 to 3 incisions per ear, alternating samples in a random fashion.

Using the above procedures adhesive bandages of the invention were tested and their hemostatic effect (i.e., the number of seconds for visible bleeding to stop) was recorded in Table I.

In order to carry out the above test procedure for hemostasis, it is necesary to look through the backing of the particular adhesive bandage which is being tested in order to observe the blood flow, i.e., to tell when bleeding has stopped. Because some types of commercially available adhesive bandages have backings which are opaque and not transparent, and come in different sizes and shapes, they were modified for test purposes. This was done by using the same Delnet covered absorbent pads as are used commercially, but where necessary combining them with a different, albeit still commercially used, adhesive backing, and forming them into a ¾ inch size adhesive bandage using the normal high-speed production techniques and equipment, even if that is not their customary size. Thus a "sheer vinyl backing" or a "tricot" backing was always used as the adhesive backing for test purposes. These backings were used with three different pads, i.e., with the 4-fold pads used commercially in BAND-AID* Brand Vinyl Adhesive Bandages (made from wood pulp and rayon) (Pad A); with the pads used in BAND-AID* Brand vinyl backed spots and juniors (a unitized pad made from 100% rayon) (Pad B); and with the pads used in BAND-AID* Brand flexible fabric adhesive bandage tricot mesh (a unitized pad made from 90% polypropylene-10% rayon) (Pad C). All the pads had a Delnet P-530 perforated polyethylene film wound release cover.

Various runs were made to obtain the hemostatic adhesive bandages (which contained an approximate 7% target add-on of Polyox Resin WSR-301), which adhesive bandages were then tested against identical non-Polyox containing adhesive bandage as a control. Usually 12 adhesive bandages from each production run were used in each test. Using pooled data (from some 40–106 samples tested for each of Pads A, B and C) the following results were obtained:

RABBIT EAR HOMOSTASIS TEST

| Pad Type | Bleeding Time (seconds) | Standard Deviation (seconds) |
|---|---|---|
| A - Control | 76.7 | 18.0 |
| A - With Polyox | 49.5 | 20.9 |
| B - Control | 67.9 | 10.7 |
| B - With Polyox | 40.5 | 20.5 |
| C - Control | 71.8 | 16.6 |
| C - With Polyox | 48.3 | 15.6 |

The hemostatis effect of the dressings of Examples 6–9 was evaluated by the same general procedures described above. As is apparent, the hemostatic adhesive bandage of the present invention has a statistically significant hemostatic effect.

What is claimed:

1. In an adhesive bandage of the type used on minor cuts and wounds, which consists of a pressure-sensitive adhesive coated backing having attached thereto an absorbent pad bandage portion covered with a perforated plastic film wound release cover, the improvement comprising:
   a very thin coating comprising a polyethylene oxide having a molecular weight of at least 600,000, on said wound release cover, thereby to improve the hemostatic effect of said adhesive bandage.

2. The adhesive bandage of claim 1, wherein the polyethylene oxide has a molecular weight of at least 4,000,000.

3. The adhesive bandage of claim 2, wherein the add-on weight of the polyethylene oxide is from 1%–10% of the weight of the perforated plastic film wound release cover to which it is added.

4. The adhesive bandage of claim 3, wherein the add-on weight of the polyethylene oxide is from 2%–8% of the weight of the perforated plastic film wound release cover.

5. The adhesive bandage of claim 3, wherein the wound release cover is made from polyethylene, polypropylene or polyester perforated plastic film.

6. The adhesive bandage of any of claims 1–5 in sterile form.

7. A hemostatic adhesive bandage comprising a backing material, a pressure-sensitive adhesive coating on one side of said backing material, an absorbent pad secured to said side of said backing material, a perforated film wound release cover overlying said absorbent pad, and on the outer surface of said wound release cover a very thin coating comprising polyethylene oxide having molecular weight of at least 600,000.

8. A process for improving the hemostasis effect of an adhesive bandage of the type used on minor cuts and wounds which consists of a pressure-sensitive adhesive coated backing covered with a perforated plastic film wound release cover comprising carrying out all steps otherwise used to manufacture said adhesive bandage, but additionally dissolving apolyethylene oxide having a molecular weight of at least 600,000 in a solvent, coating the resultant solution on the wound release cover, evaporating off the solvent leaving a very thin coating of polyethylene oxide on the wound release cover.

9. A process of claim 8, wherein the concentration of polyethylene oxide dissolved in the solvent is from 0.5 to 65%.

10. The process of claim 9, wherein said concentration is from 1.0 to 3.0%.

* * * * *